(12) United States Patent
Nakajima et al.

(10) Patent No.: US 11,957,455 B2
(45) Date of Patent: Apr. 16, 2024

(54) BIOINFORMATION ACQUIRING APPARATUS, BIOINFORMATION ACQUIRING METHOD, AND NON-TRANSITORY RECORDING MEDIUM

(71) Applicant: CASIO COMPUTER CO., LTD., Tokyo (JP)

(72) Inventors: Mitsuyasu Nakajima, Mizuho-machi (JP); Kouichi Nakagome, Tokorozawa (JP); Takashi Yamaya, Fussa (JP); Yasushi Maeno, Ome (JP); Akira Hamada, Sagamihara (JP); Shinichi Matsui, Hamura (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 303 days.

(21) Appl. No.: 17/029,466

(22) Filed: Sep. 23, 2020

(65) Prior Publication Data

US 2021/0085217 A1  Mar. 25, 2021

(30) Foreign Application Priority Data

Sep. 24, 2019  (JP) ................ 2019-172838

(51) Int. Cl.
*A61B 5/11* (2006.01)
*A61B 5/00* (2006.01)
*A61B 5/0255* (2006.01)

(52) U.S. Cl.
CPC .......... *A61B 5/1102* (2013.01); *A61B 5/0255* (2013.01); *A61B 5/7203* (2013.01); *A61B 5/7221* (2013.01); *A61B 5/7278* (2013.01)

(58) Field of Classification Search
CPC . A61B 5/1102; A61B 5/7203; A61B 5/02405; A61B 5/6892
See application file for complete search history.

(56) References Cited

U.S. PATENT DOCUMENTS

2019/0076084 A1  3/2019  Kanegae et al.
2019/0290156 A1*  9/2019  Shimauchi ............. A61B 5/352

FOREIGN PATENT DOCUMENTS

JP        2014036800 A  *  2/2014
WO   WO-2010067297 A1  *  6/2010  ............. A61B 5/024
WO   WO 2017/141976 A1     8/2017

* cited by examiner

*Primary Examiner* — Christopher A Flory
*Assistant Examiner* — Ranjani Mari Sundaresan
(74) *Attorney, Agent, or Firm* — Scully, Scott, Murphy & Presser, P.C.

(57) ABSTRACT

A bioinformation acquiring apparatus includes at least one processor and a memory configured to store a program to be executed in the processor. The processor acquires a waveform signal representing vibrations of a target, the vibrations resulting from heartbeats of the target; extracts provisional heartbeat timings from the acquired waveform signal based on a first time window; the provisional heartbeat timings indicating provisional values of heartbeat timings being timings at which the heartbeats of the target occur; acquires corrective peak timings from the acquired waveform signal based on a second time window having a shorter time length than the first time window, each of the corrective peak timings serving as a discrete correction unit for correction of the provisional heartbeat timings; corrects the extracted provisional heartbeat timings into definitive heartbeat timings based on the acquired corrective peak timings; and acquires bioinformation on the heartbeats of the target based on the corrected heartbeat timings.

8 Claims, 7 Drawing Sheets

BIOINFORMATION ACQUIRING APPARATUS, BIOINFORMATION ACQUIRING METHOD, AND NON-TRANSITORY RECORDING MEDIUM

CROSS-REFERENCE TO RELATED APPLICATION

This application claims the benefit of Japanese Patent Application No. 2019-172838, filed on Sep. 24, 2019, the entire disclosure of which is incorporated by reference herein.

FIELD

This application relates to a bioinformation acquiring apparatus, a bioinformation acquiring method, and a non-transitory recording medium.

BACKGROUND

Various systems have been developed that acquire bioinformation, such as heartbeat intervals (R-R intervals: RRI), and thus determine the health state or sleep state. In general, the bioinformation on heartbeats, such as heartbeat intervals, is acquired from electrocardiogram. The acquisition of electrocardiogram requires electrodes attached to the body of a human subject or a measurement device carried by the human subject. This requirement prohibits ready acquisition of electrocardiogram. In contrast, some techniques relate to an apparatus for acquiring bioinformation, such as heartbeat intervals, without acquisition of electrocardiogram. For example, International Publication No. WO 2017/141976 discloses a sleep state measurement apparatus that calculates transfer characteristics of ballistocardiogram and estimates an inverse transfer function, thereby acquiring a waveform corresponding to electrocardiogram from the ballistocardiogram waveform.

SUMMARY

A bioinformation acquiring apparatus of this application includes at least one processor and a memory configured to store a program to be executed in the processor. The processor acquires a waveform signal representing vibrations of a target, the vibrations resulting from heartbeats of the target; extracts provisional heartbeat timings from the acquired waveform signal based on a first time window; the provisional heartbeat timings indicating provisional values of heartbeat timings being timings at which the heartbeats of the target occur; acquires corrective peak timings from the acquired waveform signal based on a second time window having a shorter time length than the first time window, each of the corrective peak timings serving as a discrete correction unit for correction of the provisional heartbeat timings; corrects the extracted provisional heartbeat timings into definitive heartbeat timings based on the acquired corrective peak timings; and acquires bioinformation on the heartbeats of the target based on the corrected heartbeat timings.

BRIEF DESCRIPTION OF THE DRAWINGS

A more complete understanding of this application can be obtained when the following detailed description is considered in conjunction with the following drawings, in which.

DETAILED DESCRIPTION

Embodiments of the disclosure will now be described with reference to the accompanying drawings. In these drawings, the components identical to or corresponding to each other are provided with the same reference symbol.

Embodiment 1

Figure 1:
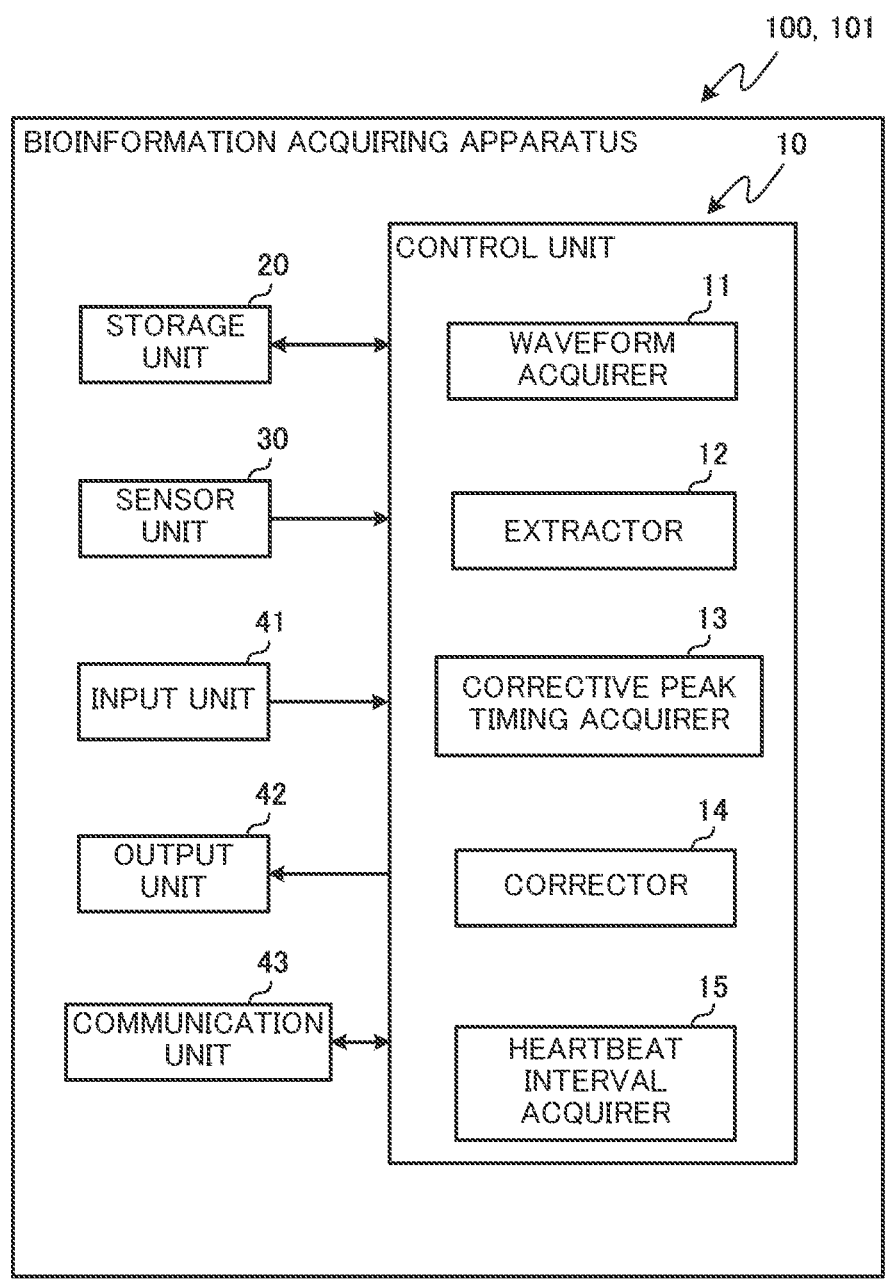
FIG. 1 illustrates an exemplary configuration of a bioinformation acquiring apparatus according to Embodiment 1.

A bioinformation acquiring apparatus 100 according to Embodiment 1 acquires heartbeat intervals of a human subject as bioinformation from a ballistocardiogram (BCG) waveform. With reference to FIG. 1, the bioinformation acquiring apparatus 100 has a functional configuration including a control unit 10, a storage unit 20, a sensor unit 30, an input unit 41, an output unit 42, and a communication unit 43.

The control unit 10 includes at least one processor, such as a central processing unit (CPU). The control unit 10 executes programs stored in the storage unit 20 and thereby achieves functions of the individual components (a waveform acquirer 11, an extractor 12, a corrective peak timing acquirer 13, a corrector 14, and a heartbeat interval acquirer 15), which will be described later. The control unit 10 also has a clocking function (not shown) using a timer (or clock) included in the CPU.

The storage unit 20 includes memories, such as a read only memory (ROM) and a random access memory (RAM). The ROM preliminarily stores the programs to be executed by the CPU of the control unit 10 and data necessary for execution of the programs. The RAM stores data, which is generated or altered during execution of the programs.

Figure 2:
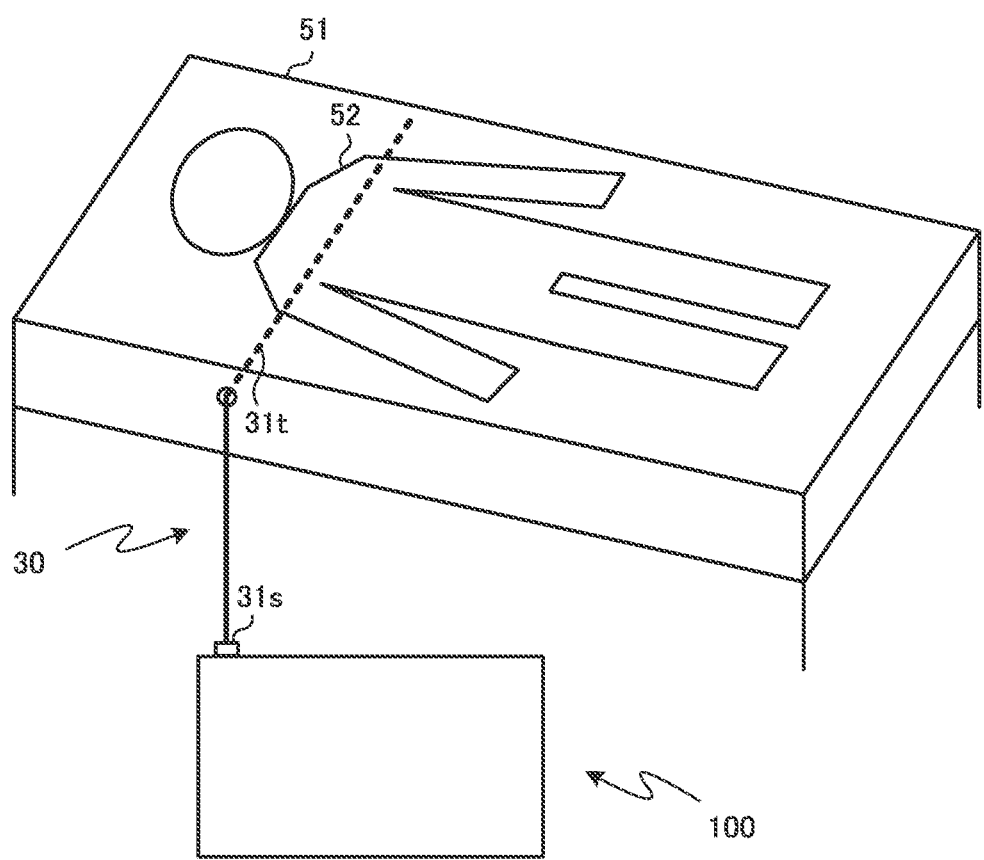
FIG. 2 illustrates a positional relationship between a lying human subject and a tube included in a sensor unit.

The sensor unit 30 includes a sensor for detecting body vibrations, and thus detects biosignals (ballistocardiogram signals in the embodiment) for acquiring bioinformation (heartbeat intervals in the embodiment) from a portion of a target (human subject in the embodiment). Specifically, as illustrated in FIG. 2, the sensor unit 30 is equipped with a tube 31t extending under a mattress 51 on which the target lies, and a sensor 31s for detecting an air pressure in the tube 31t. While the target is lying on the mattress 51, the sensor 31s detects the air pressure in the tube and can thus acquire the detected air pressure as ballistocardiogram signals representing the ballistocardiogram waveform of the target. The ballistocardiogram signals can be acquired because the air pressure detected by the sensor 31s varies depending on body vibrations of the target resulting from heartbeats of the target. The tube 31t may also extend on or inside the mattress 51, instead of under the mattress 51.

In order to acquire ballistocardiogram signals, movements of the body around the scapulae of a human subject 52 should be captured in general. The tube 31t is therefore disposed at a position corresponding to the vicinity of the scapulae of the human subject 52 lying on the mattress 51.

The configuration illustrated in FIG. 2 includes only one tube but may include two or more tubes (in the case of two or more tubes, the configuration further includes sensors corresponding to the respective tubes). The component for capturing body vibrations of the human subject 52 resulting from heartbeats should not necessarily be a tube and may be a piezoelectric element disposed under the matless, which serves as a sensor included in the sensor unit 30 in place of the tube. The sensor unit 30 should not necessarily be provided to a mattress and may be installed in a chair, for example. In an exemplary case of the sensor unit 30 installed in the chair, the bioinformation acquiring apparatus 100 is able to acquire ballistocardiogram signals of the human subject 52 sitting on the chair.

The input unit 41 includes, for example, a keyboard, a mouse, or a touch panel. The input unit 41 is an interface for receiving a user operation. A typical example of the user operation is an instruction to start or end the acquisition of bioinformation, such as heartbeat intervals.

The output unit 42 includes, for example, a liquid crystal display (LCD) or an electroluminescence (EL) display. The output unit 42 displays bioinformation, such as heartbeat intervals, acquired by the bioinformation acquiring apparatus 100, for example.

The communication unit 43 is a communication interface for transmitting and receiving data and the like to and from other external devices. The communication interface may perform wireless or wired communication. The bioinformation acquiring apparatus 100 is able to transmit the acquired bioinformation, for example, to an external server via the communication unit 43.

The functional configuration of the control unit 10 of the bioinformation acquiring apparatus 100 will now be described. The control unit 10 achieves the functions of the waveform acquirer 11, the extractor 12, the corrective peak timing acquirer 13, the corrector 14, and the heartbeat interval acquirer 15, so as to acquire bioinformation (heartbeat intervals in the embodiment) on the target (human subject in the embodiment).

Figure 3:
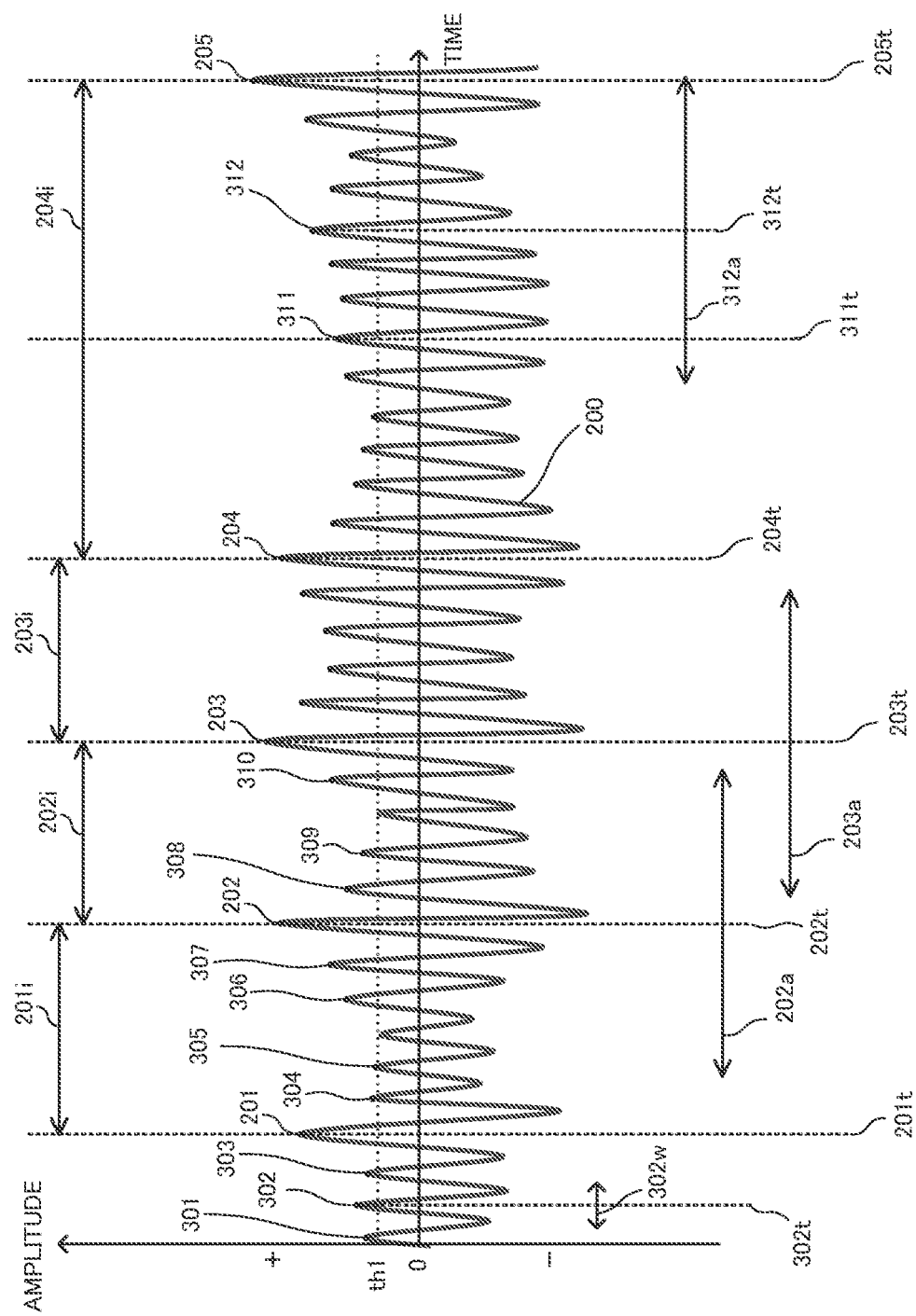
FIG. 3 illustrates an exemplary data array of ballistocardiogram signals.

Based on the value (air pressure) detected by the sensor included in the sensor unit 30, the waveform acquirer 11 acquires the air pressure as ballistocardiogram signals, and stores the air pressure and the time of detection in association with each other into the storage unit 20, thereby acquiring a ballistocardiogram waveform. Specifically, the waveform acquirer 11 samples ballistocardiogram signals output from the sensor included in the sensor unit 30 at a sampling frequency (for example, 100 Hz) and thus acquires a ballistocardiogram waveform 200 as illustrated in FIG. 3. The sampling frequency should not necessarily be 100 Hz and may be any frequency provided that the ballistocardiogram waveform can be acquired. A typical sampling frequency is approximately 80 to 100 Hz.

The extractor 12 extracts heartbeat timings from the ballistocardiogram waveform acquired by the waveform acquirer 11. The heartbeat timings indicate timings of occurrence of heartbeats. In this embodiment, the time interval between two heartbeat timings temporally adjacent to each other is acquired as a heartbeat interval.

Accordingly, the acquisition of the heartbeat intervals with high accuracy requires exact determination of heartbeat timings. The actual heartbeat timings, however, cannot be readily determined from the ballistocardiogram waveform, because the ballistocardiogram waveform contains not only the waveform of heartbeats of the target but also the waveform resulting from resonant vibrations of the body with heartbeats (that is, the waveform resulting from the eigenfrequency of the body).

In this embodiment, provisional values of heartbeat timings (hereinafter referred to as "provisional heartbeat timings") are first extracted based on the peak timings having a relatively large cycle (approximately one second) in the ballistocardiogram waveform. If provisional values of heartbeat intervals (hereinafter referred to as "provisional heartbeat intervals") calculated from the extracted provisional heartbeat timings are outliers (unexpected values out of the normal range), the extraction of provisional heartbeat timings is determined to have any dropout or error. This determination is followed by addition or deletion of a provisional heartbeat timing and correction of the provisional heartbeat timings based on the peak timings having a relatively small cycle (approximately one-sixth second) in the ballistocardiogram waveform (that is, a discrete optimization explained later). These steps can achieve estimation of the actual heartbeat timings.

In the extraction of each provisional heartbeat timing, the extractor 12 detects the maximum amplitude within a time window (hereinafter referred to as the "first time window") having a first duration and having the focused timing at the center, while shifting the focused timing along the ballistocardiogram waveform in the time axis direction. If the timing corresponding to the detected maximum amplitude accords with this focused timing, the extractor 12 extracts this focused timing as a provisional heartbeat timing. The "timing corresponding to the maximum amplitude" indicates the timing (time) at which a sampling point on the ballistocardiogram waveform has the maximum amplitude. The maximum amplitude within the first time window is a local maximum value within the range defined by the first time window, and thus is also called a first local maximum amplitude.

If an actual heartbeat timing is assumed at the center of the first time window, the first duration is defined such that the previous and subsequent actual heartbeat timings immediately before and immediately after the actual heartbeat timing are close to the start edge and the end edge of the first time window but not encompassed in the first time window. That is, the first duration is defined to be twice as long as the assumed minimum heartbeat interval. For example, if the maximum heart rate of the human subject is assumed to be 100 per minute, the first duration is 1.2 seconds (2×60 seconds÷100=1.2 seconds). The first duration of 1.2 seconds is appropriate in the case of acquisition of heartbeat intervals from a human subject during sleep (because a human subject in good health is not supposed to have a heart rate exceeding 100 per minute during sleep). The first duration can be varied depending on a target subject.

In FIG. 3, the description now focuses on a point 202 representing a sampled ballistocardiogram signal. Since the peak value of the ballistocardiogram signals within the first time window having a duration 202a is represented by the point 202, the timing (peak timing) of occurrence of a ballistocardiogram signal represented by the point 202 is extracted as a provisional heartbeat timing 202t. Also, the timing of occurrence of a ballistocardiogram signal represented by a point 203 is also extracted as a provisional heartbeat timing 203t. In contrast, for example, if attention is focused on a point 312, the peak value of the ballistocardiogram signal within the first time window having a duration 312a is represented by not the point 312 but a point 205. A timing 312t of occurrence of a ballistocardiogram signal represented by the point 312 is therefore not extracted as a provisional heartbeat timing.

The corrective peak timing acquirer 13 acquires each of a plurality of correcting timings, each of the plurality of correcting timings serves as a discrete correction unit for correction of provisional heartbeat timings, from the ballistocardiogram waveform acquired by the waveform acquirer 11. The ballistocardiogram waveform contains at least a first waveform resulting from heartbeats (strokes) and a second waveform resulting from the eigenfrequency (approximately 6 Hz) of the human body (trunk). Because of the shorter cycle of the second waveform than that of the first waveform, the provisional heartbeat timings extracted based on the peak timings of the first waveform (peak timings having a longer cycle) may be deviated from the actual heartbeat timings due to the effects of the peak timings of the second waveform (that is, the peak timings having a shorter cycle). These deviations of the provisional heartbeat timings are determined depending on the peak timings of the second waveform. Specifically, in the case where a provisional heartbeat timing extracted from the ballistocardiogram waveform is deviated from the actual heartbeat timing, the true timing is expected to be any of the peak timings of the second waveform located before and after the peak timing of the first waveform on the time axis. Based on this expectation, the corrective peak timing acquirer 13 acquires peak timings of the second waveform, which serve as correcting timings (discrete correction units) for correction of provisional heartbeat timings.

Specifically, the corrective peak timing acquirer 13 extracts the maximum amplitude of the ballistocardiogram waveform within a time window (second time window) having the focused timing at the center, while shifting the focused timing along the ballistocardiogram waveform in the time axis direction. The second time window has a duration equal to or smaller than the inverse (approximately one-sixth second) of the eigenfrequency of the human body (trunk). If the maximum amplitude is a first threshold th1 or higher and if the timing corresponding to this maximum amplitude is not located at an end of the second time window, then the corrective peak timing acquirer 13 acquires the timing corresponding to the maximum amplitude as a corrective peak timing. If the timing corresponding to the maximum amplitude is located at an end of the second time window, a larger amplitude is expected to exist outside the end of the second time window (that is, the true peak timing is expected to be found by shifting the focused timing). In this case, the corrective peak timing acquirer 13 does not acquire the timing corresponding to the maximum amplitude as a corrective peak timing. The maximum amplitude within the second time window is a local maximum value within the range defined by the second time window, and thus is also called a second local maximum amplitude.

The second time window is required to have a duration (time length) equal to or smaller than the inverse of the eigenfrequency of the subject body. In this embodiment, the duration is 0.1 second (that is, ten sampling points per second), for example. An exemplary value of the first threshold is equal to the one fifth of the average of the first local maximum amplitudes in the entire ballistocardiogram waveform.

The description now focuses on a point 302, which is one of the sampling points on the ballistocardiogram waveform illustrated in FIG. 3. The point 302 has the maximum amplitude of the ballistocardiogram waveform within the second time window having a duration 302w, and the amplitude at the point 302 is the first threshold th1 or higher.

The corrective peak timing acquirer 13 thus acquires a timing 302t of the point 302 as a corrective peak timing to be used for correction of provisional heartbeat timings. Also, the corrective peak timing acquirer 13 acquires, as corrective peak timings, the timings of points 301, 303, 201, 304, 305, 306, 307, 202, 308, 309, 310, 203, and the like. Each of the corrective peak timings is the timing of which the maximum amplitude is equal to or higher than the first threshold th1 within the second time window.

The corrector 14 corrects the provisional heartbeat timings extracted by the extractor 12, using the corrective peak timings acquired by the corrective peak timing acquirer 13 as correction units. This correcting step will be explained in detail later.

The heartbeat interval acquirer 15 acquires, as a heartbeat interval, the time interval between two adjacent heartbeat timings, which are adjacent to each other, after correction, based on the provisional heartbeat timings corrected by the corrector 14.

The above description focuses on the functional configuration of the bioinformation acquiring apparatus 100. A heartbeat interval acquiring process of the bioinformation acquiring apparatus 100 will now be explained with reference to FIG. 4. If the bioinformation acquiring apparatus 100 receives an instruction to start the heartbeat interval acquiring process from a user via the input unit 41, the bioinformation acquiring apparatus 100 starts the heartbeat interval acquiring process. The user of the bioinformation acquiring apparatus 100 may be or may not be identical to the human subject in the heartbeat interval acquiring process.

The waveform acquirer 11 of the bioinformation acquiring apparatus 100 first causes the sensor unit 30 to acquire a ballistocardiogram waveform (Step S101). In general, Step S101 is repeated continuously during a biosignal acquisition period (for example, the period from when the human subject 52, who is the target of acquisition of heartbeat interval, goes to bed (lies on the mattress) until when the human subject 52 gets up). While the step S101 is being repeated, the waveform acquirer 11 stores the detected values (ballistocardiogram signals) acquired from the sensor unit 30 in association with the times (timings) of detection in the chronological order into the storage unit 20. FIG. 3 illustrates a ballistocardiogram waveform defined by plotting these detected values on a graph. In Step S101, the waveform acquirer 11 needs not to be informed of the exact time when the human subject goes to bed or gets up, and may operate during a biosignal acquisition period (for example, from 23 to 7 o'clock) set by a simple timer function. Alternatively, the biosignal acquisition period may be set in accordance with instructions (instructions to start and end the acquisition of ballistocardiogram waveform) from the input unit 41.

The waveform acquirer 11 then applies a bandpass filter (BPF) to the acquired ballistocardiogram waveform (multiple detected values acquired from the sensor unit 30) (Step S102). The bandpass filter allows signals in the frequency band of 4 to 10 Hz to pass therethrough, for example. This bandpass filter is aimed at removing noise in the frequency band higher than 10 Hz and the frequency band lower than 4 Hz and therefore does not allow for passage of frequency components higher than 10 Hz and frequency components lower than 4 Hz. In particular, the removal of frequency components lower than 4 Hz leads to removal of DC components and noise components caused by respiration. In the case of no need for removal of noise in the frequency band higher than 10 Hz, the bandpass filter may be replaced with a highpass filter (HPF) that allows for passage of signals in the frequency band of 4 Hz or higher, for example. In the case of no need for removal of noise in both the frequency band higher than 10 Hz and the frequency band lower than 4 Hz, the waveform acquirer 11 may skip Step S102.

FIG. 3 illustrates an exemplary ballistocardiogram waveform after the BPF process using the bandpass filter (or highpass filter) in Step S102. The ballistocardiogram waveform contains not only the waveform (first waveform of approximately 1 Hz) resulting from heartbeats but also the waveform (second waveform of approximately 6 Hz) resulting from the eigenfrequency of the human body (trunk). Because of the BPF process of filtering the multiple detected values acquired from the sensor unit 30 using the bandpass filter, the second waveform is outstanding in the ballistocardiogram waveform illustrated in FIG. 3.

The extractor 12 then extracts first local maximum amplitudes from the ballistocardiogram waveform after the BPF process using the above-mentioned first time window, and extracts the timings corresponding to the extracted first local maximum amplitudes as provisional heartbeat timings (Step S103).

The corrective peak timing acquirer 13 then extracts second local maximum amplitudes from the ballistocardiogram waveform, and acquires the timings corresponding to the extracted second local maximum amplitudes as corrective peak timings (Step S104).

The corrector 14 then calculates provisional heartbeat intervals based on the provisional heartbeat timings extracted by the extractor 12, determines whether the calculated provisional heartbeat intervals contain any outlier, and adds or deletes a provisional heartbeat timing if any outlier is contained (Step S105). Each of the calculated provisional heartbeat intervals indicates a time interval between two provisional heartbeat timings temporally adjacent to each other. The time interval between a certain provisional heartbeat timing and the subsequent provisional heartbeat timing immediately after is defined as the provisional heartbeat interval associated with the certain provisional heartbeat timing. The outlier indicates an unexpected value of heartbeat interval out of the normal range.

The configuration in this embodiment uses the ratio (level of deviation) between the provisional heartbeat interval and an averaged neighborhood heartbeat interval for determining an outlier, followed by addition or deletion of a provisional heartbeat timing based on this ratio. The averaged neighborhood heartbeat interval indicates the average of the provisional heartbeat intervals associated with the provisional heartbeat timings, which include the focused provisional heartbeat timing and the provisional heartbeat timings in the neighborhood (for example, in the range of five minutes before and after the focused provisional heartbeat timing).

For example, with reference to FIG. 3, the provisional heartbeat interval associated with the provisional heartbeat timing 201t is a provisional heartbeat interval 201i, which is the time interval between the provisional heartbeat timing 201t and the subsequent provisional heartbeat timing 202t. Also, the provisional heartbeat interval associated with the provisional heartbeat timing 202t is a provisional heartbeat interval 202i, which is the time interval between the provisional heartbeat timing 202t and the subsequent provisional heartbeat timing 203t. In an exemplary case where the focused provisional heartbeat timing is the provisional heartbeat timing 203t, the averaged neighborhood heartbeat interval can be obtained by calculating the average of provisional heartbeat intervals in the neighborhood of the provisional heartbeat timing 203t (for example, in the range of five minutes before and after the provisional heartbeat timing 203t). In this case, the averaged neighborhood heartbeat interval associated with the provisional heartbeat timing is obtained by calculating the average of provisional heartbeat intervals within a certain range having the provisional heartbeat timing 203t at the center, which encompasses the provisional heartbeat interval 201i and the provisional heartbeat interval 202i. The certain range in calculation of the averaged neighborhood heartbeat interval is only required to encompass the focused provisional heartbeat timing and does not necessarily have the focused provisional heartbeat timing at the center.

The corrector 14 obtains the averaged neighborhood heartbeat interval for each provisional heartbeat timing. Based on the ratio between the provisional heartbeat interval associated with this provisional heartbeat timing and the averaged neighborhood heartbeat interval, the corrector 14 adds or deletes a provisional heartbeat timing. In short, in the case of an excessively long provisional heartbeat interval relative to the averaged neighborhood heartbeat interval, the corrector 14 adds a new provisional heartbeat timing to divide the provisional heartbeat interval into short segments. In the case of an excessively short provisional heartbeat interval, the corrector 14 deletes the provisional heartbeat timing to provide a long provisional heartbeat interval. This process can reduce the effects brought about by a provisional heartbeat timing that the extractor 12 failed to extract due to noise or the like and by a provisional heartbeat timing that the extractor 12 erroneously extracted.

Specifically, for example, if this provisional heartbeat interval is equal to or larger than the product of the averaged neighborhood heartbeat interval and the first reference value (for example, 1.5), then the corrector 14 divides this provisional heartbeat interval by the number of divisions. The number of division is the value calculated by dividing this provisional heartbeat interval by the averaged neighborhood heartbeat interval and rounding off the fractional portion. The corrector 14 adds a new provisional heartbeat timing at the corrective peak timing that is closest to each divisional timing. The divisional timing indicates a timing obtained by dividing the period from the provisional heartbeat timing associated with the divided provisional heartbeat interval to the subsequent provisional heartbeat timing by the number of divisions.

In contrast, if this provisional heartbeat interval is smaller than the product of the averaged neighborhood heartbeat interval and the second reference value (for example, 0.5), then the corrector 14 deletes the subsequent provisional heartbeat timing immediately after this provisional heartbeat timing (that is, the provisional heartbeat timing corresponding to the end of this provisional heartbeat interval). If the provisional heartbeat interval is still smaller than the product of the averaged neighborhood heartbeat interval and 0.5 even after deletion of the single provisional heartbeat timing, then the corrector 14 continues to delete the subsequent provisional heartbeat timing immediately after this provisional heartbeat timing until the provisional heartbeat interval becomes equal to or larger than the product of the averaged neighborhood heartbeat interval and 0.5. The corrector 14 may delete this provisional heartbeat timing instead of deleting the subsequent provisional heartbeat timing immediately after the provisional heartbeat timing.

Figure 5:
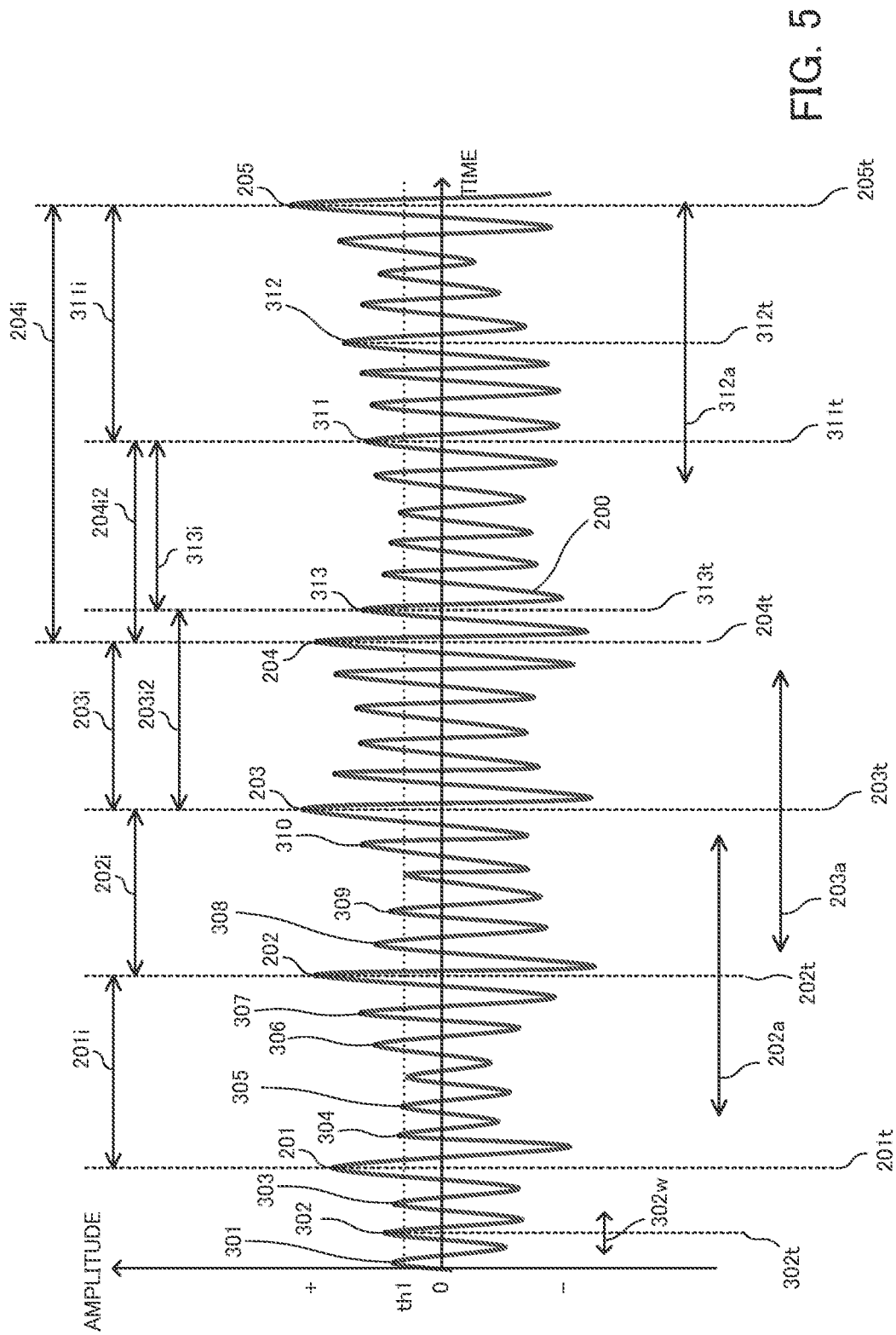
FIG. 5 is a diagram for explaining correction of provisional heartbeat timings.

For example, in FIG. 3, a provisional heartbeat interval 204i is approximately twice as long as the averaged neighborhood heartbeat interval (which is not shown but is expected to have the duration similar to that of the provisional heartbeat interval 201*i* or the like). The corrector 14 therefore divides the provisional heartbeat interval 204*i* into half by adding a new provisional heartbeat timing 311*t* at a timing of a point 311, which is one of the corrective peak timings. The provisional heartbeat interval 204*i* is thus divided into a provisional heartbeat interval 204*i*2 and a provisional heartbeat interval 311*i*, as illustrated in FIG. 5. In the example illustrated in FIG. 3, the division illustrated in FIG. 5 can make each of the provisional heartbeat intervals equal to a value calculated by multiplying the averaged neighborhood heartbeat interval by a value of 0.5 or larger and smaller than 1.5. The processing thus completes Step S105 and goes to Step S106. If any other excessively long or excessively short provisional heartbeat interval exists, the corrector 14 repeats Step S105 until all the provisional heartbeat intervals are made equal to a value calculated by multiplying the averaged neighborhood heartbeat interval by a value of 0.5 or larger and smaller than 1.5.

The corrector 14 then executes a discrete optimization (explained later), thereby correcting the provisional heartbeat timings into definitive heartbeat timings (Step S106). The heartbeat interval acquirer 15 determines definitive heartbeat intervals, by calculating, for each two heartbeat timings adjacent to each other among the definitive heartbeat timings, the time interval between these two heartbeat timings (Step S107), and then terminates the heartbeat interval acquiring process. After the determination of definitive heartbeat intervals in Step S107, the heartbeat interval acquirer 15 may output the determined intervals to the output unit 42, transmit the intervals via the communication unit 43 to an external device, or store the intervals into the storage unit 20.

The above explanation focuses on the heartbeat interval acquiring process. In this process, the order of Steps S103 and S104 may be reversed, for example. That is, the process may be executed in the order of Steps S102, S104, S103, and S105. The discrete optimization (Step S106) involved in the heartbeat interval acquiring process will now be explained with reference to FIG. 6.

The corrector 14 first calculates adjacent heartbeat interval differences for all the provisional heartbeat timings, and sorts the provisional heartbeat timings in the descending order of adjacent heartbeat interval difference, which begins from the provisional heartbeat timing having the largest adjacent heartbeat interval difference, and then stores the sorted provisional heartbeat intervals into the storage unit 20 (Step S201). The adjacent heartbeat interval difference indicates the absolute value of the difference between a previous interval and a subsequent interval. The previous interval indicates a period from the previous provisional heartbeat timing immediately before the provisional heartbeat timing (hereinafter referred to as "focused provisional heartbeat timing") on which attention is focused, to the focused provisional heartbeat timing. The subsequent interval indicates a period from the focused provisional heartbeat timing to the subsequent provisional heartbeat timing immediately after the focused provisional heartbeat timing. For example, in FIG. 3, the adjacent heartbeat interval difference at the provisional heartbeat timing 202*t* is represented by abs(203*t*−202*t*−(202*t*−201*t*))=abs(202*i*−201*i*). The function abs returns the absolute value of the argument.

The corrector 14 then reads the provisional heartbeat timings in the sorted order in Step S201 (that is, the descending order of adjacent heartbeat interval difference) (Step S202). The corrector 14 then tries to displace each of the read provisional heartbeat timings temporally forward or rearward, so as to make the adjacent heartbeat interval difference as small as possible (Step S203). The corrector 14 uses the corrective peak timings as discrete correction units (that is, does not correct the provisional heartbeat timing into a timing other than the corrective peak timings) in the correction of the provisional heartbeat timing in Step S203. If the adjacent heartbeat interval difference after the correction is smaller than that before the correction, the corrector 14 determines successful correction. In contrast, if the adjacent heartbeat interval difference after the correction is equal to or larger than that before the correction, the corrector 14 determines unsuccessful correction, and does not correct the provisional heartbeat timing (or restores the provisional heartbeat timing after the correction to the provisional heartbeat timing before the correction).

For example, with reference to FIG. 5, the adjacent heartbeat interval difference associated with a provisional heartbeat timing 204*t* is represented by abs(204*i*2−203*i*). If the abs(313*i*−203*i*2) is smaller than the value abs(204*i*2−203*i*), the corrector 14 corrects the provisional heartbeat timing 204*t* into a provisional heartbeat timing 313*t* (successful correction). In contrast, if the value abs(204*i*2−203*i*) is smaller than the value abs(313*i*−203*i*2), the corrector 14 does not correct the provisional heartbeat timing 204*t* (unsuccessful correction). In FIG. 5, in the case of focusing on the provisional heartbeat timing 204*t* and using the corrective peak timings as discrete correction units, the adjacent heartbeat interval difference is apparently larger than the value abs(204*i*2−203*i*) even after the correction of the provisional heartbeat timing 204*t* into a corrective peak timing other than the provisional heartbeat timing 313*t*. If the correction in Step S203 fails for all the provisional heartbeat timings read in the sorted order, the provisional heartbeat timings are regarded as definitive heartbeat timings.

The corrector 14 then determines whether the correction in Step S203 is successful (Step S204). If the correction is successful (Step S204; Yes), the processing returns to Step S201 and restarts from the sorting based on the adjacent heartbeat interval difference again. If the correction is unsuccessful (Step S204; No), the corrector 14 determines whether the ballistocardiogram waveform contains any subsequent provisional heartbeat timing in the sorted order in Step S201 (Step S205).

If the ballistocardiogram waveform contains any subsequent provisional heartbeat timing (Step S205; Yes), the processing returns to Step S202. If the ballistocardiogram waveform contains no subsequent provisional heartbeat timing (Step S205; No), which means completion of correction of all the provisional heartbeat timings, then the processing exits the discrete optimization and returns to Step S107 of the heartbeat interval acquiring process.

The above-explained discrete optimization can achieve optimization of all the provisional heartbeat timings using the corrective peak timings so as to achieve the smallest adjacent heartbeat interval differences, and can cause a corrective peak timing, which the extractor 12 failed to extract as a provisional heartbeat timing, to be regarded as a definitive heartbeat timing. This configuration can acquire heartbeat intervals with high accuracy and high robustness even from a ballistocardiogram waveform on which various types of noise are superimposed. In addition, the extractor 12 extracts provisional heartbeat timings using the first time window and can thus achieve extraction of the provisional heartbeat timings in a cycle close to the normal heartbeat interval, thereby reducing the possibility of occurrence of outliers of heartbeat interval. Furthermore, the corrective peak timing acquirer 13 acquires corrective peak timings using the second time window and can thus achieve highly accurate acquisition of the peak timings of a waveform resulting from the eigenfrequency of the body. In addition, the corrector 14 determines an outlier of heartbeat interval based on a representative neighborhood heartbeat interval and can thus achieve highly accurate determination of an outlier, leading to highly accurate addition and deletion of a provisional heartbeat timing.

Embodiment 2

All the provisional heartbeat timings have equal priorities regardless of their amplitudes in the discrete optimization (FIG. 6) according to Embodiment 1. In another idea, a provisional heartbeat timing of a heartbeat having a larger amplitude may be more likely to be the true heartbeat timing. The following description focuses on Embodiment 2, which involves a discrete optimization modified based on this idea.

Figure 4:
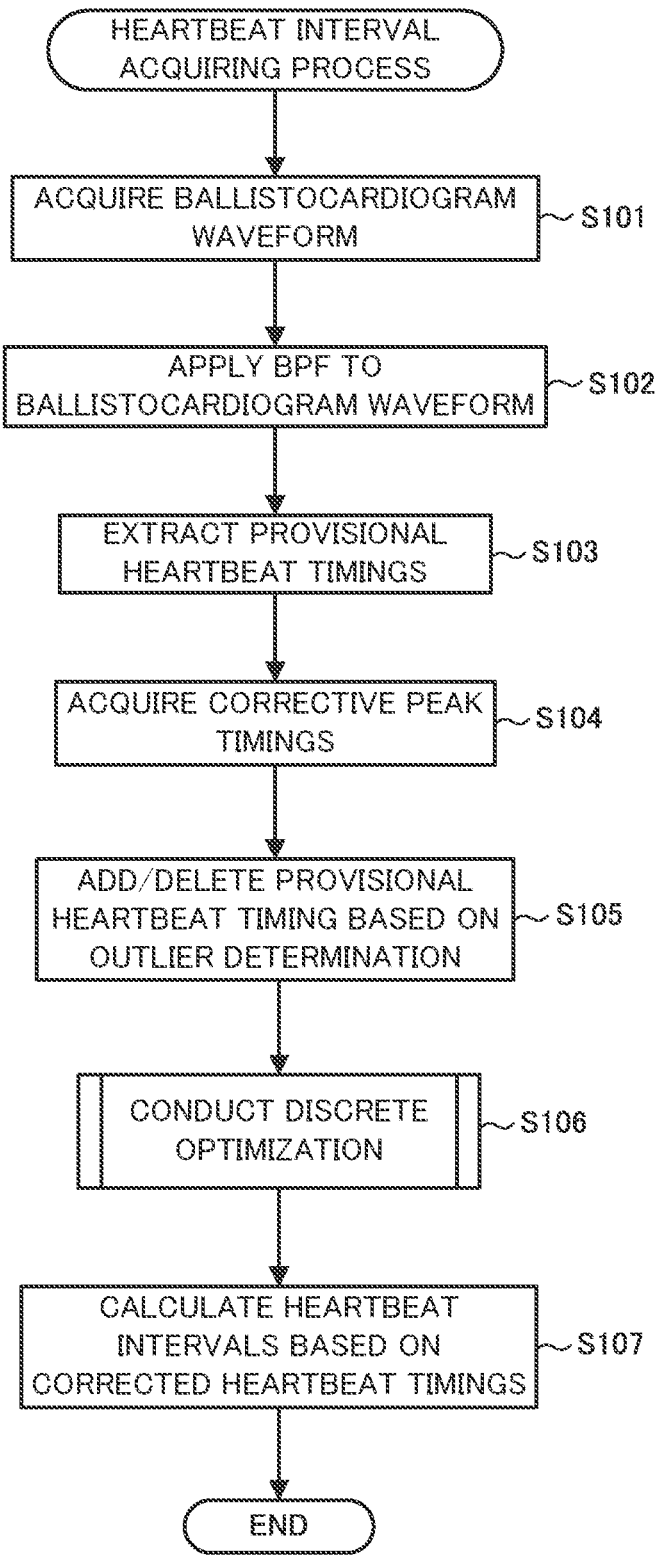
FIG. 4 is a flowchart of a heartbeat interval acquiring process according to Embodiment 1.

A bioinformation acquiring apparatus 101 according to Embodiment 2 has the functional configuration identical to the functional configuration of the bioinformation acquiring apparatus 100 according to Embodiment 1, as illustrated in FIG. 1. Also, the bioinformation acquiring apparatus 101 according to Embodiment 2 executes the heartbeat interval acquiring process identical to the heartbeat interval acquiring process in the bioinformation acquiring apparatus 100 according to Embodiment 1, as illustrated in FIG. 4. It should be noted that a discrete optimization invoked in Step S106 of the heartbeat interval acquiring process according to Embodiment 2 differs from the discrete optimization (FIG. 6) according to Embodiment 1. The discrete optimization in the bioinformation acquiring apparatus 101 will now be explained with reference to FIG. 7.

The corrector 14 first calculates evaluation scores D for each of all the provisional heartbeat timings with reference to the expression (1) below (the corrector 14 calculates an evaluation score D for each provisional heartbeat timing), sorts the provisional heartbeat timings in the descending order of evaluation score D, which begins from the provisional heartbeat timing having the largest evaluation score D, and then stores the sorted provisional heartbeat timings into the storage unit 20 (Step S301):

(Evaluation score $D$)=(adjacent heartbeat interval difference)÷(amplitude adjustment value)    (1)

It should be noted that the adjacent heartbeat interval difference is identical to that described in Embodiment 1. The amplitude adjustment value indicates the product of the amplitude of the ballistocardiogram waveform at the focused provisional heartbeat timing and an adjustment factor K. An exemplary value of the adjustment factor K is equal to the inverse of the average of the amplitudes at all the provisional heartbeat timings.

The corrector 14 then reads the provisional heartbeat timings in the sorted order in Step S301 (that is, the descending order of evaluation score D) (Step S302). The corrector 14 then determines whether the evaluation score D of each of the read provisional heartbeat timings is larger than a second threshold th2 (Step S303). An exemplary value of the second threshold is equal to the half of the average of all the adjacent heartbeat interval differences.

If the evaluation score D is the second threshold or lower (Step S303; No), the corrector 14 determines completion of the discrete optimization and terminates the discrete optimization. If the discrete optimization is terminated without the correction in Step S304, the provisional heartbeat timings are regarded as definitive heartbeat timings. If the evaluation score D is higher than the second threshold (Step S303; Yes), the corrector 14 tries to correct this provisional heartbeat timing read in Step S302 so as to make the adjacent heartbeat interval difference as small as possible (Step S304). This step is identical to Step S203 in FIG. 6 according to Embodiment 1.

The corrector 14 then determines whether the correction in Step S304 is successful (Step S305). If the correction is successful (Step S305; Yes), the processing returns to Step S301 and restarts from the sorting based on the evaluation score D again. If the correction is unsuccessful (Step S305; No), the corrector 14 determines whether the ballistocardiogram waveform contains any subsequent provisional heartbeat timing in the sorted order in Step S301 (Step S306).

If the ballistocardiogram waveform contains any subsequent provisional heartbeat timing (Step S306; Yes), the processing returns to Step S302. If the ballistocardiogram waveform contains no subsequent provisional heartbeat timing (Step S306; No), which means completion of correction of all the provisional heartbeat timings, then the processing exits the discrete optimization and returns to Step S107 of the heartbeat interval acquiring process.

The above-explained discrete optimization can achieve optimization of all the provisional heartbeat timings using the corrective peak timings so as to make the evaluation scores D equal to the second threshold or lower. This configuration can acquire heartbeat intervals with high accuracy and high robustness even from a ballistocardiogram waveform on which various types of noise are superimposed, as in Embodiment 1.

Modification of Embodiment 2

Although the amplitude adjustment value indicates the "product of the amplitude of the ballistocardiogram waveform at the focused provisional heartbeat timing and the adjustment factor K" in the expression (1) for calculating an evaluation score D according to Embodiment 2, this amplitude adjustment value is only an example. Alternatively, the amplitude adjustment value may be the difference between the amplitude of the ballistocardiogram waveform at the focused provisional heartbeat timing and the amplitude of the ballistocardiogram waveform at a corrective peak timing adjacent to this provisional heartbeat timing, for example. It should be noted that two differences are calculated because of two amplitudes at the adjacent corrective peak timings on both sides of (immediately before and immediately after) the focused provisional heartbeat timing. The amplitude adjustment value may be the average of the two differences, the larger one of the two differences, or the smaller one of the two differences. Alternatively, the amplitude adjustment value may be the product of this difference (any of the average, larger one, and smaller one) and an adjustment factor L. An exemplary value of the adjustment factor L is calculated by determining the difference between the amplitude at each corrective peak timing and the amplitude at the subsequent corrective peak timing immediately after this corrective peak timing, averaging the differences for all the corrective peak timings on the ballistocardiogram waveform, and obtaining the inverse of the average.

Other Modifications

According to the above-described embodiments, the addition and deletion of a provisional heartbeat timing are conducted based on the ratio between the provisional heartbeat interval associated with each focused timing and the averaged neighborhood heartbeat interval in Step S105 of the heartbeat interval acquiring process (FIG. 4). The value to be compared with the provisional heartbeat interval associated with the focused timing, however, may be other representative value than the averaged neighborhood heartbeat interval. For example, the addition and deletion of a provisional heartbeat timing may be conducted based on the ratio between the provisional heartbeat interval associated with the focused timing and the neighborhood heartbeat interval median (median of provisional heartbeat intervals in the neighborhood of the focused timing). The average or median of provisional heartbeat intervals in the neighborhood of the focused timing is also referred to as "representative neighborhood heartbeat interval".

Step S105 is not a necessary step and may be skipped. Step S105 may be replaced with other general step for removing outliers of heartbeat interval so as to achieve addition and deletion of provisional heartbeat timings.

Although the evaluation score D is compared with the second threshold th2 in Step S303 of the discrete optimization (FIG. 7) according to Embodiment 2, this comparison is not a necessary step. The corrector 14 may skip Step S303. In this configuration, Step S302 is followed by Step S304.

Figure 6:
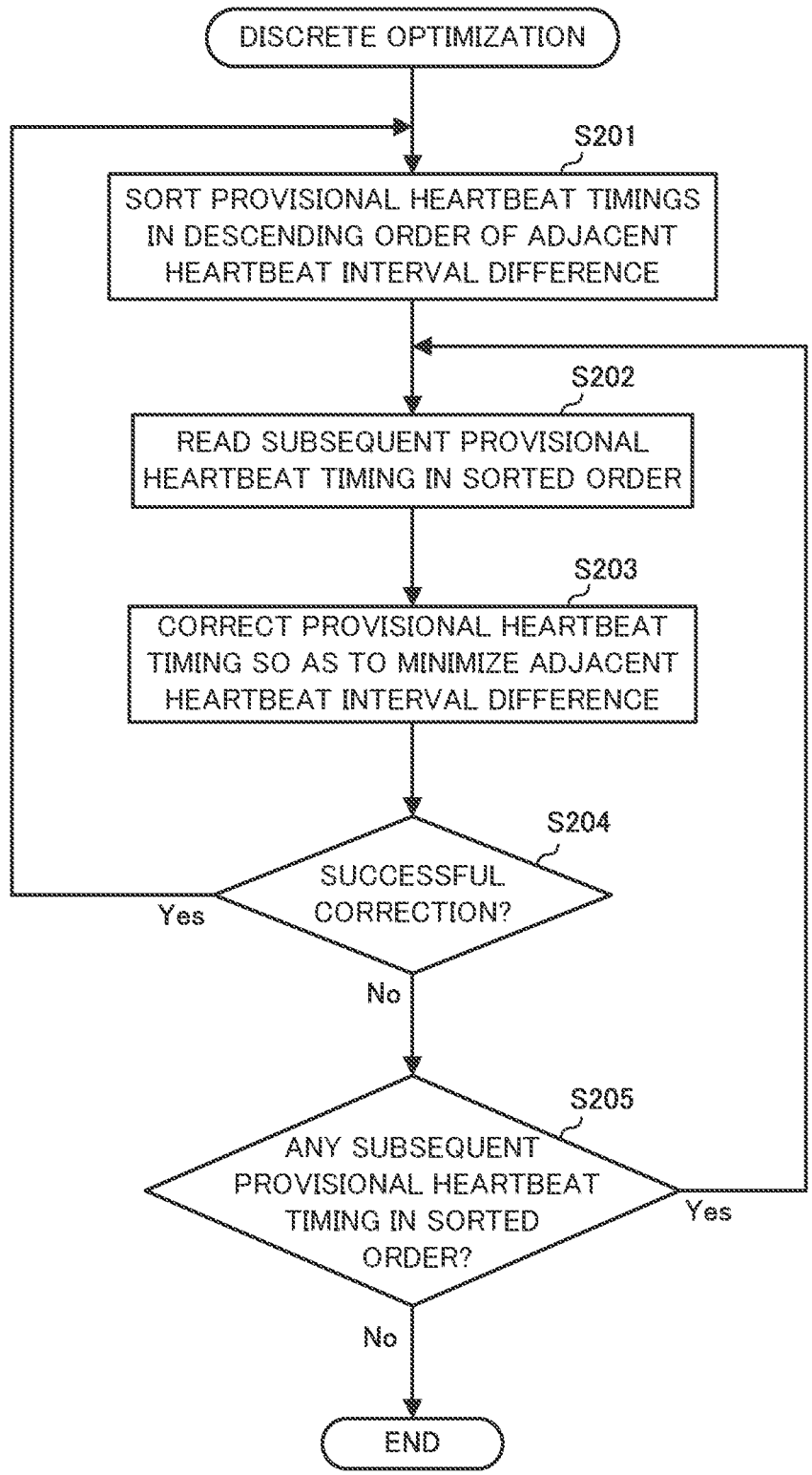
FIG. 6 is a flowchart of a discrete optimization according to Embodiment 1.
Figure 7:
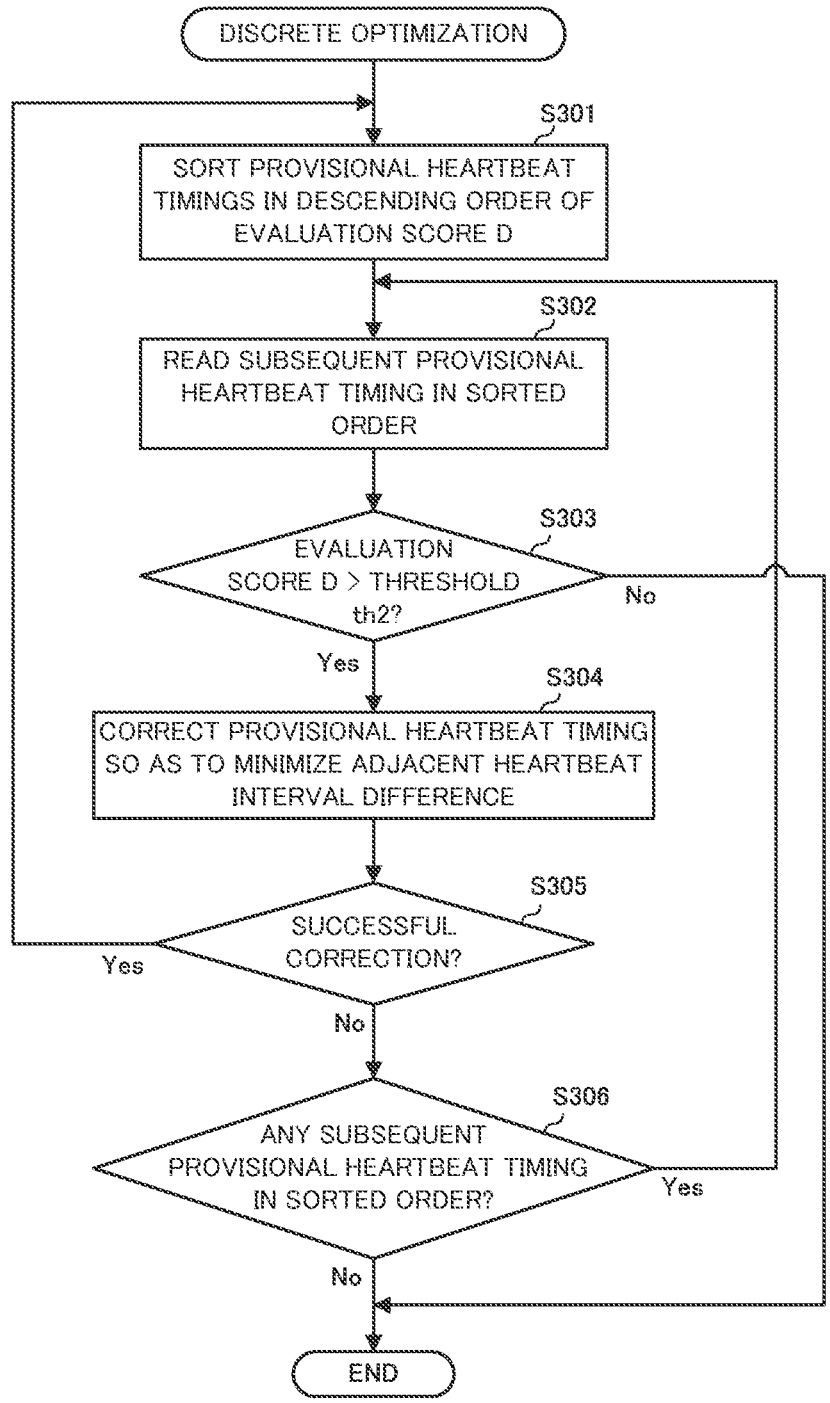
FIG. 7 is a flowchart of a discrete optimization according to Embodiment 2.

Alternatively, in Embodiment 1, the adjacent heartbeat interval difference may be compared with a third threshold th3 in a step between Steps S202 and S203 of the discrete optimization (FIG. 6). In this configuration, the discrete optimization may be terminated if the adjacent heartbeat interval difference is the third threshold or lower. The third threshold may be defined in any manner. An exemplary value of the third threshold is equal to the half of the average of all the adjacent heartbeat interval differences.

According to the above-described embodiments, the discrete optimization involves correcting a provisional heartbeat timing into a corrective peak timing so as to achieve the smallest adjacent heartbeat interval difference, and regarding the corrected heartbeat timing as a definitive heartbeat timing. This correction step, however, is only an example. For example, the provisional heartbeat timing may be corrected into a corrective peak timing so as to achieve a smaller adjacent heartbeat interval difference instead of the smallest adjacent heartbeat interval difference. Alternatively, the provisional heartbeat timing may be corrected into a corrective peak timing so as to achieve a small (for example, smallest) value of any evaluation score (for example, the above-described evaluation score D) calculated from the adjacent heartbeat interval difference, for example. This correction should not be limited to replacement of the provisional heartbeat timing with a corrective peak timing. Any correction based on corrective peak timings may be performed (for example, the provisional heartbeat timing may be corrected into the timing corresponding to the average of the corrective peak timing and this provisional heartbeat timing).

According to the above-described embodiments, the waveform acquirer 11 acquires a ballistocardiogram waveform and acquires heartbeat intervals based on the ballistocardiogram waveform. Alternatively, the waveform used for acquisition of bioinformation, such as heartbeat intervals may be a waveform other than the ballistocardiogram waveform. The waveform acquirer 11 may acquire not only the ballistocardiogram waveform but also waveform signals representing vibrations of the target resulting from heartbeats. In this configuration, the waveform signals acquired by the waveform acquirer 11 may be used by the bioinformation acquiring apparatus 100 or 101 to acquire bioinformation.

According to the above-described embodiments, the extractor 12 extracts heartbeat timings (provisional heartbeat timings), which are used as references for acquisition of heartbeat intervals. Alternatively, the extractor 12 may extract other timings in a broader sense (for example, timings of pulses) other than heartbeat timings, depending on a type of ballistocardiogram waveform acquired by the waveform acquirer 11 or a type of bioinformation acquired by the bioinformation acquiring apparatus 100 or 101.

According to the above-described embodiments, the ballistocardiogram waveform for one night, that is, from when the human subject goes to bed until when the human subject gets up, is acquired in Step S101 of the heartbeat interval acquiring process (FIG. 4). The data for one night, however, should not necessarily be acquired. The processing may go to Step S102 after acquisition of data for a certain period (for example, one hour), followed by the above-explained operations using the data (for example, data for one hour) that is acquired thus far, go to Step S107, and then return to Step S101, so as to repeat the heartbeat interval acquiring process every certain period.

According to the above-described embodiments, the bioinformation acquiring apparatus 100 or 101 includes the input unit 41, the output unit 42, and the communication unit 43. These components, however, are not essential components and may be excluded from the bioinformation acquiring apparatus 100 or 101. In an exemplary case where the bioinformation acquiring apparatus 100 or 101 acquires a waveform (for example, a ballistocardiogram waveform) representing vibrations of the target resulting from heartbeats via the communication unit 43 from an external sensor device or the like, the bioinformation acquiring apparatus 100 or 101 must include the communication unit 43 but may exclude the sensor unit 30.

According to the above-described embodiments, the bioinformation acquiring apparatus 100 or 101 acquires heartbeat intervals of a human subject. Alternatively, the acquisition target may also be a general animal, such as dog, cat, horse, cow, pig, or chicken, other than a human. The sensor unit 30 can also acquire a waveform containing the waveform resulting from heartbeats of the animal and the waveform resulting from the eigenfrequency of the body of the animal, so that the discrete optimization can be conducted based on the eigenfrequency of the body of the animal.

Although the bioinformation to be acquired is heartbeat intervals according to the above-described embodiments, the bioinformation may be information other than the heartbeat intervals. The bioinformation acquiring apparatus 100 or 101 may acquire bioinformation related to heartbeats of the target (for example, a heart rate, pulse intervals, beat-to-beat intervals (BBIs), or information on fluctuations in heartbeats) through a discrete optimization.

The individual functions of the bioinformation acquiring apparatus 100 or 101 can also be achieved by a computer, such as a general personal computer (PC). Specifically, in the above-described embodiments, the programs for the processes, such as the heartbeat interval acquiring process, executed by the bioinformation acquiring apparatus 100 or 101 are preliminarily stored in the ROM of the storage unit 20. Alternatively, these programs may be stored in a non-transitory computer-readable recording medium, such as a flexible disk, a compact disc read only memory (CD-ROM), a digital versatile disc (DVD), a magneto-optical disc (MO), a memory card, or a universal serial bus (USB) memory to be distributed. These programs on the recording medium may be read and installed in the computer, so that the computer can achieve the functions of the bioinformation acquiring apparatus 100 or 101.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

What is claimed is:

1. A bioinformation acquiring apparatus comprising:
at least one processor configured to:
receive a ballistocardiogram waveform, detected by a sensor, the ballistocardiogram waveform including at least a first waveform resulting from heartbeats and a second waveform resulting from eigenfrequency of a body, the second waveform having a shorter cycle than the first waveform;
extract provisional heartbeat timings from the ballistocardiogram waveform from a first time window having a focused timing while shifting the focused timing of the first time window along the ballistocardiogram waveform in a time axis direction;
acquire corrective peak timings from the ballistocardiogram waveform from a second time window having a focused timing while shifting the focused timing of the second time window along the ballistocardiogram in the time axis direction, the second time window having a duration shorter than a duration of the first time window, and the duration of the second time window being equal to or smaller than an inverse of the eigenfrequency of the body;
calculate an adjacent heartbeat interval difference for each of the provisional heartbeat timings, the adjacent heartbeat interval difference indicating a level of deviation between a previous interval and a subsequent interval, the previous interval indicating a period from a previous provisional heartbeat timing immediately before the each of the provisional heartbeat timing to the each of the provisional heartbeat timing, and the subsequent interval indicating a period from the each of the provisional heartbeat timing to a subsequent provisional heartbeat timing immediately after the each of the provisional heartbeat timing;
correct the provisional heartbeat timings into definitive heartbeat timings by adding a new provisional heartbeat timing at a timing of one of the corrective peak timings and/or deleting one of the provisional heartbeat timings so as to reduce the adjacent heartbeat interval difference; and
acquire heartbeat intervals based on the definitive heartbeat timings.

2. The bioinformation acquiring apparatus according to claim 1,
wherein the at least one processor is configured to:
detect a maximum amplitude within the first time window having focused timing at a center of the first time window;
in a case in which a timing corresponding to the maximum amplitude detected accords with the focused timing of the first time window, extract the timing corresponding to the maximum amplitude detected as one of the provisional heartbeat timings, and
in a case in which a timing corresponding to the maximum amplitude detected does not accord with the focused timing of the first time window, not extract the timing corresponding to the maximum amplitude detected as one of the provisional heartbeat timings.

3. The bioinformation acquiring apparatus according to claim 1,
wherein the at least one processor is configured to:
detect a second maximum amplitude from the ballistocardiogram waveform using the second time window; and
acquire a timing corresponding to the second maximum amplitude as one of the corrective peak timings.

4. The bioinformation acquiring apparatus according to claim 1,
wherein the at least one processor is configured to:
calculate a provisional heartbeat interval as a period from one of the provisional heartbeat timings to the subsequent provisional heartbeat timing based on the provisional heartbeat timings; and
for the each of the provisional heartbeat timings,
calculate a representative neighborhood heartbeat interval indicating a representative value of the provisional heartbeat intervals in a neighborhood of the provisional heartbeat timing; and
delete the provisional heartbeat timing or add the new provisional heartbeat timing based on a level of deviation between the provisional heartbeat interval and the representative neighborhood heartbeat interval.

5. The bioinformation acquiring apparatus according to claim 4,
wherein the at least one processor is configured to:
if the ballistocardiogram waveform has any provisional heartbeat timing associated with the provisional heartbeat interval equal to or larger than a product of the representative neighborhood heartbeat interval and a first reference value, add, between the provisional heartbeat timing and the subsequent provisional heartbeat timing, the new provisional heartbeat timing.

6. The bioinformation acquiring apparatus according to claim 4,
wherein the at least one processor is configured to:
if the ballistocardiogram waveform has any provisional heartbeat timing associated with the provisional heartbeat interval smaller than a product of the representative neighborhood heartbeat interval and a second reference value, delete the provisional heartbeat timing or the subsequent provisional heartbeat timing.

7. A bioinformation acquiring method comprising:
receiving a ballistocardiogram waveform, detected by a sensor, the ballistocardiogram waveform including at least a first waveform resulting from heartbeats and a second waveform resulting from eigenfrequency of a body, the second waveform having a shorter cycle than the first waveform;
extracting provisional heartbeat timings from the ballistocardiogram waveform from a first time window having a focused timing while shifting the focused timing of the first time window along the ballistocardiogram waveform in a time axis direction;

acquiring corrective peak timings from the ballistocardiogram waveform from a second time window having a focused timing while shifting the focused timing of the second time window having a duration shorter than a duration of the first time window, and the duration of the second time window being equal to or smaller than an inverse of the eigenfrequency of the body;

calculating an adjacent heartbeat interval difference for each of the provisional heartbeat timings, the adjacent heartbeat interval difference indicating a level of deviation between a previous interval and a subsequent interval, the previous interval indicating a period from a previous provisional heartbeat timing immediately before the each of the provisional heartbeat timing to the each of the provisional heartbeat timing, and the subsequent interval indicating a period from the each of the provisional heartbeat timing to a subsequent provisional heartbeat timing immediately after the each of the provisional heartbeat timing;

correcting the provisional heartbeat timings into definitive heartbeat timings by adding a new provisional heartbeat timing at a timing of one of the corrective peak timings and/or deleting one of the provisional heartbeat timings so as to reduce the adjacent heartbeat interval difference; and acquiring heartbeat intervals based on the definitive heartbeat timings.

8. A non-transitory recording medium storing a program that causes a computer to at least execute:

receive a ballistocardiogram waveform, detected by a sensor, the ballistocardiogram waveform including at least a first waveform resulting from heartbeats and a second waveform resulting from eigenfrequency of a body, the second waveform having a shorter cycle than the first waveform;

extract provisional heartbeat timings from the ballistocardiogram waveform from a first time window having a focused timing while shifting the focused timing of the first time window along the ballistocardiogram waveform in a time axis direction;

acquire corrective peak timings from the ballistocardiogram waveform from a second time window having a focused timing while shifting the focused timing of the second time window along the ballistocardiogram in the time axis direction, the second time window having a duration shorter than a duration of the first time window, and the duration of the second time window being equal to or smaller than an inverse of the eigenfrequency of the body;

calculate an adjacent heartbeat interval difference for each of the provisional heartbeat timings, the adjacent heartbeat interval difference indicating a level of deviation between a previous interval and a subsequent interval, the previous interval indicating a period from a previous provisional heartbeat timing immediately before the each of the provisional heartbeat timing to the each of the provisional heartbeat timing, and the subsequent interval indicating a period from the each of the provisional heartbeat timing to a subsequent provisional heartbeat timing immediately after the each of the provisional heartbeat timing;

correct the provisional heartbeat timings into definitive heartbeat timings by adding a new provisional heartbeat timing at a timing of one of the corrective peak timings and/or deleting one of the provisional heartbeat timings so as to reduce the adjacent heartbeat interval difference; and acquire heartbeat intervals based on the definitive heartbeat timings.

* * * * *